US008755892B2

(12) United States Patent
Amurthur et al.

(10) Patent No.: US 8,755,892 B2
(45) Date of Patent: Jun. 17, 2014

(54) SYSTEMS FOR STIMULATING NEURAL TARGETS

(75) Inventors: Badri Amurthur, Edina, MN (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1099 days.

(21) Appl. No.: 11/749,500

(22) Filed: May 16, 2007

(65) Prior Publication Data

US 2008/0288016 A1 Nov. 20, 2008

(51) Int. Cl.
*A61N 1/04* (2006.01)
*A61N 1/36* (2006.01)

(52) U.S. Cl.
CPC .................................. *A61N 1/36017* (2013.01)
USPC ................. 607/44; 607/2; 607/136; 607/149

(58) Field of Classification Search
USPC ......................... 607/44, 55–57, 136, 118, 137
See application file for complete search history.

(56) References Cited

U.S. PATENT DOCUMENTS

| | | | |
|---|---|---|---|
| 4,503,863 A | | 3/1985 | Katims |
| 4,865,048 A | | 9/1989 | Eckerson |
| 4,966,164 A | * | 10/1990 | Colsen et al. .................... 607/72 |
| 4,989,605 A | | 2/1991 | Rossen |
| 5,197,471 A | | 3/1993 | Otero |
| 5,263,480 A | | 11/1993 | Wernicke et al. |
| 5,458,625 A | | 10/1995 | Kendall |
| 5,514,175 A | | 5/1996 | Kim et al. |
| 5,556,421 A | | 9/1996 | Prutchi et al. |
| 5,673,692 A | * | 10/1997 | Schulze et al. ................. 600/301 |
| 5,891,181 A | | 4/1999 | Zhu |
| 6,473,644 B1 | | 10/2002 | Terry, Jr. et al. |
| 7,218,964 B2 | | 5/2007 | Hill et al. |
| 7,277,761 B2 | | 10/2007 | Shelchuk |
| 7,536,227 B1 | * | 5/2009 | Poore et al. ..................... 607/118 |
| 2002/0072781 A1 | | 6/2002 | Lattner et al. |

(Continued)

FOREIGN PATENT DOCUMENTS

| | | |
|---|---|---|
| JP | 54-070685 A | 6/1979 |
| JP | 7-116190 A | 5/1995 |

(Continued)

OTHER PUBLICATIONS

"International Application Serial No. PCT/US2008/006023, Invitation to Pay Additional Fees and Partial International Search Report mailed Aug. 5, 2008", 6 pgs.

(Continued)

*Primary Examiner* — Kennedy Schaetzle
*Assistant Examiner* — Erica Lee
(74) *Attorney, Agent, or Firm* — Schwegman Lundberg & Woessner, P.A.

(57) ABSTRACT

Disclosed herein, among other things, is a method for stimulating neural targets in the vicinity of a human ear. According to an embodiment, a device is clipped on a patient ear lobe, the device including a neural stimulation electrode. A neural stimulation signal is applied to the electrode to transcutaneously stimulate neural targets in the vicinity of the ear lobe, according to an embodiment. A physiological parameter is sensed using a sensor connected to the device. According to an embodiment, the neural stimulation signal is adjusted in response to the sensed parameter. The method is used is a variety of treatment regimens, including anti-hypertensive and cardiac improvement therapy.

20 Claims, 8 Drawing Sheets

(56) References Cited

U.S. PATENT DOCUMENTS

| | | | |
|---|---|---|---|
| 2002/0091418 A1 | 7/2002 | Hauser et al. |
| 2002/0107553 A1 | 8/2002 | Hill et al. |
| 2002/0143369 A1 | 10/2002 | Hill et al. |
| 2002/0165586 A1 | 11/2002 | Hill et al. |
| 2003/0195588 A1 | 10/2003 | Fischell et al. |
| 2004/0215289 A1 | 10/2004 | Fukui |
| 2005/0102006 A1 | 5/2005 | Whitehurst et al. |
| 2005/0143779 A1 | 6/2005 | Libbus |
| 2005/0165460 A1 | 7/2005 | Erfan |
| 2006/0041283 A1 | 2/2006 | Gelfand et al. |
| 2006/0122675 A1 | 6/2006 | Libbus et al. |

FOREIGN PATENT DOCUMENTS

| | | | |
|---|---|---|---|
| JP | 8-322825 A | 12/1996 |
| JP | 11-500930 A | 1/1999 |
| JP | 2003-511163 A | 3/2003 |
| JP | 2003511163 A | 3/2003 |
| JP | 2003-520094 A | 7/2003 |
| JP | 2003-325636 A | 11/2003 |
| JP | 2004180988 | 7/2004 |
| JP | 2004-275427 A | 10/2004 |
| JP | 2004533297 A | 11/2004 |
| JP | 2006524106 A | 10/2006 |
| WO | WO-9216257 | 10/1992 |
| WO | WO-9625978 A1 | 8/1996 |
| WO | WO-0126729 A1 | 4/2001 |
| WO | WO-01/52731 A1 | 7/2001 |
| WO | WO-2002096512 A1 | 12/2002 |
| WO | WO-03/076008 A1 | 9/2003 |
| WO | WO-2004/000413 A2 | 12/2003 |
| WO | WO-2004069328 | 8/2004 |
| WO | WO-2004091719 A2 | 10/2004 |
| WO | WO-2006062728 A1 | 6/2006 |
| WO | WO-2006122148 | 11/2006 |
| WO | WO-2007/134804 A1 | 11/2007 |
| WO | WO-2008/143814 A2 | 11/2008 |

OTHER PUBLICATIONS

"International Search Report and Written Opinion for Application No. PCT/US2005/042208, Date Mailed Apr. 18, 2006", 16 Pages.

Huang, H Q., et al., "Improvement of blood pressure and left cardiac function in patients with hypertension by auricular acupuncture", Zhong Xi Yi Jie He Za Zhi, vol. 11, No. 11, [Article in Chinese with English Abstract], (Nov. 1991),654-6, 643-4.

Imad, Libbus , et al., "Transcutaneous Neurostimulator for Modulating Cardiovascular Function", U.S. Appl. No. 11/548,359, filed Oct. 11, 2006, 46 pgs.

Libbus, I. , et al., "Method and Apparatus for Synchronizing Neural Simulation to Cardiac Cycles", U.S. Appl. No. 11/099,141, filed Apr. 5, 2005, 36 pgs.

Libbus, I. , et al., "System and Method for Closed-Loop Neural Stimulation", U.S. Appl. No. 10/992,319, filed Nov. 18, 2004, 50 pgs.

Nolan, James , et al., "Prospective study of heart rate variability and mortality in chronic heart failure: results of the United Kingdom heart failure evaluation and asessment of risk trial (UK-heart).", Circulation, vol. 98, No. 15, (Oct. 13, 1998),1510-1516.

Sigurdsson, Axel , "The role of neurohormonal activation in chronic heart failure and postmyocardial infarction", American Heart Journal, 132 (1 Pt 2 Su), (Jul. 1996),229-234.

Vanoli, Emilio , "Vagal stimulation and prevention of sudden death in conscious dogs with a healed myocardial infarction", Circulation Research, vol. 68, No. 5, (May 1991),1471-1481.

Zamotrinsky, A V., et al., "Vagal neurostimulation in patients with coronary artery disease", Autonomic Neuroscience-Basic & Clinical, 88(1-2), (Apr. 12, 2001),109-116.

"U.S. Appl. No. 11/005,703, Advisory Action mailed Jun. 18, 2007", 3 pgs.

"U.S. Appl. No. 11/005,703, Appeal Brief filed Jan. 9, 2008", 50 pgs.

"U.S. Appl. No. 11/005,703, Communication mailed Jul. 10, 2008", 2 pgs.

"U.S. Appl. No. 11/005,703, Examiner's Answer mailed Apr. 7, 2008", 24 pgs.

"U.S. Appl. No. 11/005,703, Final Offiice Action mailed Apr. 11, 2007", 13 pgs.

"U.S. Appl. No. 11/005,703, Non-Final Office Action mailed Nov. 8, 2006", 12 pgs.

"U.S. Appl. No. 11/005,703, Reply Brief filed Jun. 6, 2008 to Examiner's Answer mailed Apr. 7, 2008", 10 pgs.

"U.S. Appl. No. 11/005,703, Response filed Feb. 8, 2007 to Non-Final Office Action mailed Nov. 8, 2006", 26 pgs.

"U.S. Appl. No. 11/005,703, Response filed Jun. 11, 2007 to Final Office Action mailed Apr. 11, 2007", 16 pgs.

"International Application Serial No. PCT/US2008/006023, International Search Report mailed Dec. 3, 2008", 6 pgs.

"International Application Serial No. PCT/US2008/006023, Written Opinion mailed Dec. 3, 2008", 9 pgs.

"European Application Serial No. 05851959.6, Office Action mailed Apr. 23, 2010", 4 pgs.

"European Application Serial No. 05851959.6, Office Action mailed Apr. 30, 2009", 3 pgs.

"European Application Serial No. 05851959.6, Office Action mailed Nov. 24, 2008", 3 pgs.

"European Application Serial No. 05851959,6, Response filed Mar. 30, 2009 to Office Action mailed Nov. 24, 2008", 15 pgs.

"European Application Serial No. 05851959.6, Response filed Sep. 2, 2010 to Communication dated Apr. 23, 2010", 5 pgs.

"European Application Serial No. 05851959.6, Response filed Sep. 21, 2009 to Office Action mailed Apr. 30, 2009", 10 pgs.

"Japanese Application Serial No. 2007-545498, Amendment filed Nov. 20, 2008", (w/ English Translation of Amended Claims), 18 pgs.

"Japanese Application Serial No. 2007-545498, Office Action mailed Sep. 14, 2011", (w/ English Translation), 6 pgs.

"Japanese Application Serial No. 2007-545498, Office Action Response filed Mar. 12, 2012 to Office Action mailed Sep. 14, 2011", With English Claims, 20 pgs.

"Japanese Application Serial No. 2010-508384, Office Action mailed Dec. 19, 2011", (w/ English Translation), 10 pgs.

"Japanese Application Serial No. 2010-508384, Response filed Mar. 16, 2012 to Office Action mailed Dec. 19, 2011", (w/ English Translation of Amended Claims), 9 pgs.

"Japanese Application Serial No. 2010-508384, Examiners Decision of Final Refusal mailed May 17, 2012", With English Translation, 9 pgs.

"Japanese Application Serial No. 2007-545498, Examiners Decision of Final Refusal mailed Jun. 11, 2012", With English Translation, 9 pgs.

\* cited by examiner

SYSTEMS FOR STIMULATING NEURAL TARGETS

TECHNICAL FIELD

This disclosure relates generally to medical devices, and more particularly to systems and methods for stimulating neural targets in the vicinity of a human ear.

BACKGROUND

Neural stimulation has been the subject of a number of studies and has been proposed for several therapies. The autonomic system controls physiological activities of the body and the imbalance of autonomic tone is related to many diseases and conditions. Reduced autonomic balance (increase in sympathetic and decrease in parasympathetic cardiac tone) during heart failure has been shown to be associated with left ventricular dysfunction and increased mortality. Sympathetic inhibition, as well as parasympathetic activation, has been associated with reduced arrhythmia vulnerability following a myocardial infarction. Vagus nerve stimulation has been proposed to treat sleep disorders, gastrointestinal motility, eating disorders, obesity, anorexia, gastrointestinal tract disorders, hypertension, coma, and epilepsy. Direct electrical stimulation of parasympathetic nerves can activate the baroreflex, inducing a reduction of sympathetic nerve activity and reducing blood pressure by decreasing vascular resistance. Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult. However, implantation of electrodes is an invasive procedure, and it can be difficult to immediately implant electrodes after a myocardial infarction.

Neural stimulation targeting other nerves has shown similar beneficial effect. Improved systems and methods for stimulating neural targets are needed.

SUMMARY

Disclosed herein, among other things, is a device for mounting to an ear lobe of a patient. The device includes a clip adapted to detachably attach to the ear lobe, according to an embodiment. The device also includes a neural stimulator including an electrode. The neural stimulator is adapted to stimulate neural targets in the vicinity of the ear lobe. The neural stimulator is further adapted to communicate with a stimulation circuit to receive a neural stimulation signal. The device also includes a sensor adapted to monitor a physiological parameter. The device titrates therapy using the physiological parameter, according to various embodiments. In one embodiment, the sensor includes an infrared sensor. The sensor includes a pulse oximetry sensor, in an embodiment.

Disclosed herein, among other things, is a method for stimulating neural targets in the vicinity of a human ear. According to an embodiment, a device is clipped on a patient ear lobe, the device including a neural stimulation electrode. A neural stimulation signal is applied to the electrode to transcutaneously stimulate neural targets in the vicinity of the ear lobe, according to an embodiment. A physiological parameter is sensed using a sensor connected to the device. According to an embodiment, the neural stimulation signal is adjusted in response to the sensed parameter.

Disclosed herein, among other things, is a method for treatment of high blood pressure. According to an embodiment, a patient is identified who could benefit from blood pressure reduction therapy. Therapy for blood pressure reduction is delivered to the patient, including delivering neural stimulation to transcutaneously stimulate neural targets in the vicinity of the ear lobe, according to various embodiments.

Disclosed herein, among other things, is a method for cardiac function improvement treatment. According to an embodiment, a patient is identified who could benefit from cardiac function improvement therapy. Therapy for cardiac function improvement is delivered to the patient, including delivering neural stimulation to transcutaneously stimulate neural targets in the vicinity of the ear lobe, according to various embodiments.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

Figure 1A:
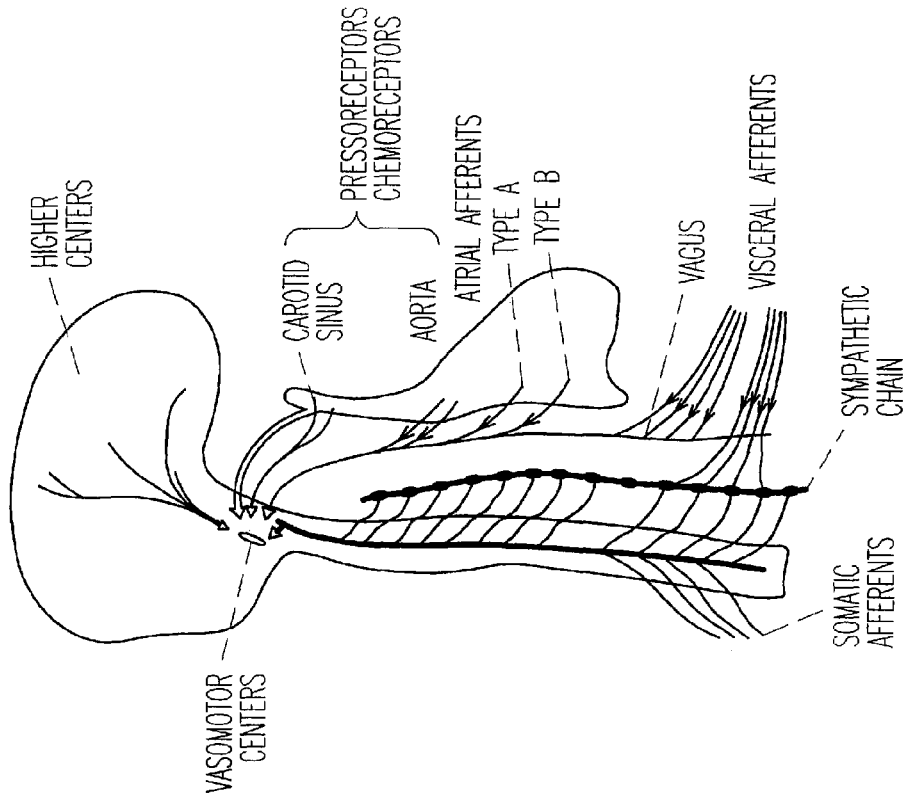
FIGS. 1A and 1B illustrate neural mechanisms for peripheral vascular control.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to an "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Various embodiments of the present subject matter are related to systems and methods for stimulating neural targets in the vicinity of a human ear. The neural stimulation can be used for treating hypertension and/or coronary artery disease by chronically lowering blood pressure. The neural stimulation can also be used for treating heart failure by improving cardiac function (cardiac function improvement therapy, or intermittent stress on the heart to improve health of the heart). The system for stimulating neural targets in the vicinity of a human ear can include a transcutaneous or implanted device, in various embodiments. Neural targets in the vicinity of the human ear include, but are not limited to, the auricular branch of the vagus nerve.

Various embodiments provide closed loop control of the neural stimulation. Some neural stimulator embodiments are integrated with a blood pressure monitor, and some sense blood pressure from the carotid artery. Other embodiments deliver the stimulation via an open loop system, such as may be provided by short term therapy, and intermittent or periodic therapies of relative short duration, for example.

Transcutaneous and some superficial subcutaneous approaches to peripheral nerve stimulation are capable of avoiding direct neural contact with a stimulating electrode, thereby reducing problems associated with neural inflammation and injury commonly associated with direct contact electrodes.

Provided below is a discussion of neural physiology. The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example. The nervous system includes afferent nerves, which transmit neural signals from the body (e.g. vascular control, body organs, and the like) to the central nervous system (CNS), and includes efferent nerves which transmit neural signals from the CNS out to the body.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Figure 1B:
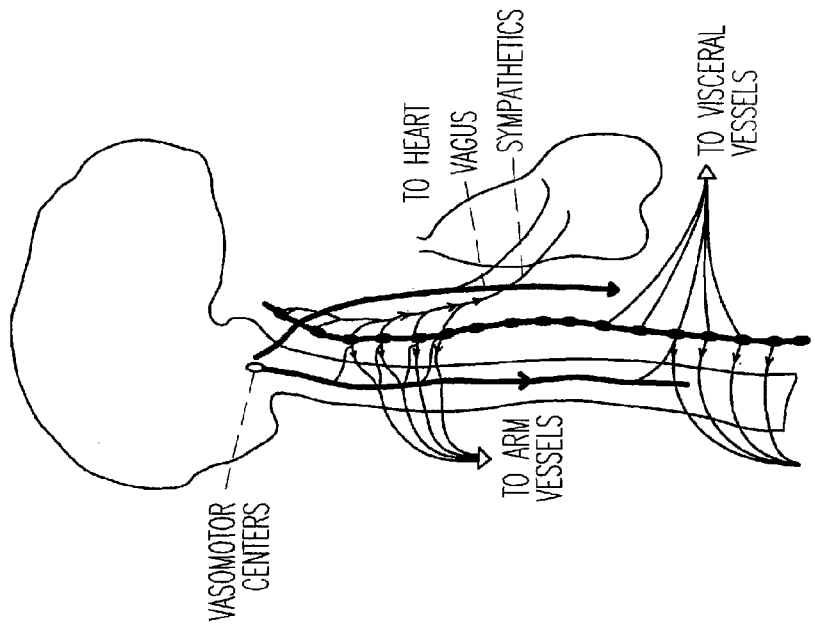

FIGS. 1A and 1B illustrate neural mechanisms for peripheral vascular control. The vagus nerve is illustrated in these figures. FIG. 1A generally illustrates afferent nerves to vasomotor centers. An afferent nerve conveys impulses toward a nerve center (CNS). A vasomotor center relates to nerves that dilate and constrict blood vessels to control the size of the blood vessels. FIG. 1B generally illustrates efferent nerves from vasomotor centers. An efferent nerve conveys impulses away from a nerve center (CNS).

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

The vagus nerve is an afferent nerve, such that the neural stimulation is transmitted to the CNS. Vagal stimulation simultaneously increases parasympathetic and decreases sympathetic activity, and is believed to prevent further remodeling or predisposition to fatal arrhythmias in post-MI patients, to help restore autonomic balance and increase HRV (heart rate variability), to increase parasympathetic and reduce sympathetic tone in hypertrophic cardiac myopathy (HCM), neurogenic hypertension, and arrhythmia protection, to reduce anginal symptoms, to increase coronary blood flow (CBF), and to prevent development of congestive heart failure (CHF) following MI.

The auricular nerve of the vagus nerve, which includes the greater auricular nerve and the lesser auricular nerve, originates from the cervical plexus. The greater auricular nerve innervates the surfaces of the outer ear, and the skin over the parotid gland and mastoid process. The parotid gland is a salivary gland found in front of the ears and that extends to the area beneath the earlobe along the lower border of the jawbone. The mastoid process is the conical prominence of the temporal bone of the human skull behind the ear.

The disclosure relates at least in part to a device for providing stimulation of neural targets near the ear lobe or ear canal for anti-hypertensive and/or cardiac function improvement. In one embodiment, the device is non-invasive. Examples include, but are not limited to, a clip-on ear lobe device (as in FIGS. 2A and 2B, for example) or ear plug (protruding into the ear canal) with a transcutaneous stimulator for chronic lowering of blood pressure or for systolic and diastolic dysfunction, improvement in left ventricular ejection fraction (LVEF), end-diastolic volume (EDV) and/or treatment of heart failure. In another embodiment, the device is implantable. Examples include, but are not limited to, a surgically implanted device in the inner ear for chronic lowering of blood pressure or for systolic and diastolic dysfunction, improvement in left ventricular ejection fraction (LVEF), end-diastolic volume (EDV) and/or treatment of heart failure. The device may be standalone, or communicate with other implanted devices such as a pacemaker, cardiac resynchronization therapy device (CRT), baroreceptor stimulator or vagal nerve stimulation device. When communicating with another device, one of the devices may control the therapy delivery in the other device, and/or the devices may exchange sensor information for therapy titration. Since acupuncture channels meet in the ear, stimulation of neural targets in the vicinity of the ear has potential applications for pain management, obesity, eating disorders, and addiction, for example.

Figure 2A:
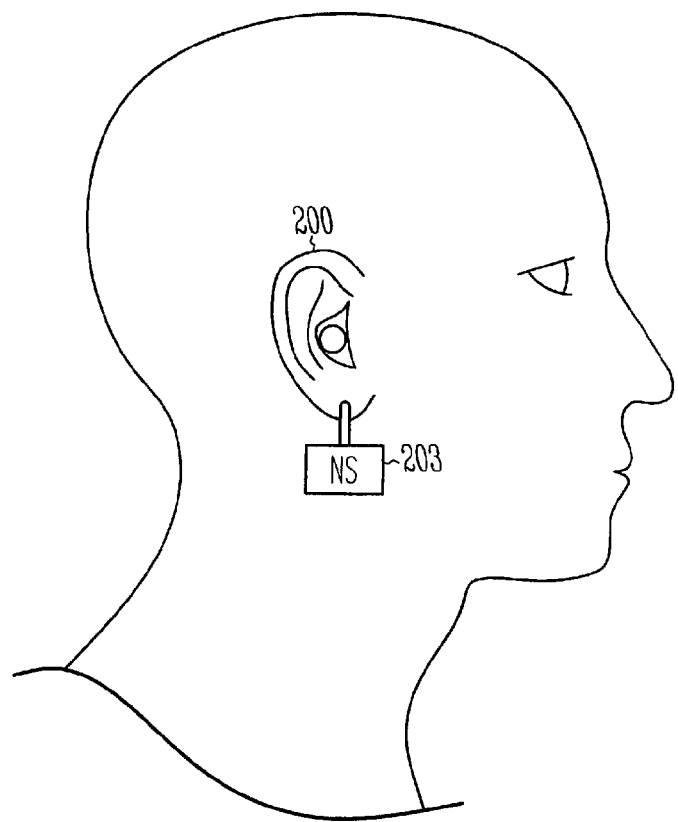
FIGS. 2A and 2B illustrate a neural stimulator with a neural stimulator electrode adapted to be clipped to an ear lobe to provide neural stimulation therapy, according to various embodiments.
Figure 2B:

FIGS. 2A and 2B illustrate a neural stimulator with a neural stimulator electrode adapted to be clipped to an ear lobe to provide neural stimulation therapy, according to various embodiments. FIG. 2A illustrates a human ear 200 and a neural stimulation device 203 with neural stimulation electrode (e.g. bipolar electrode) adapted to be clipped to the lobe of the human ear. The neural stimulation electrode is connected to the neural stimulation device. The neural stimulation device is capable of providing appropriate neural stimulation to the neural stimulation electrode to elicit depolarization of the auricular nerve branch, or other neural target in the vicinity of the ear.

According to various embodiments, the illustrated neural stimulation device 203 functions as an open loop stimulation system. In the open loop system, the neural stimulation is applied based on a predetermined or programmed set of parameters. Thus, for example, various open loop embodiments stimulate with a predetermined waveform (e.g. white noise, square, sinusoidal, triangular, and the like), magnitude, frequency, burst frequency and duration. Some embodiments provide intermittent stimulation and some embodiments provide periodic stimulation. Periodic stimulation relates to stimulation at regular intervals. Intermittent stimulation relates to applying stimulation during some times but not at other times. Intermittent stimulation does not necessarily refer to providing stimulation at regular intervals.

According to various embodiments, the illustrated neural stimulation device 203 functions as a closed loop stimulation system. In the closed loop system, physiology signals are sensed. The neural stimulation device appropriately adjusts the applied neural stimulation therapy based on the sensed physiology sensors. Examples of physiology sensors include sensors to detect heart rate and blood pressure, and further includes electrocardiogram (ECG) monitors.

FIG. 2B illustrates a neural stimulation device 203 placed on the ear lobe using a clip 210. Other types of devices are possible without departing from the scope of the disclosure. Examples include, but are not limited to, expandable, stent-like electrode placed in the auditory canal, or implanted neural electrodes or devices. Various embodiments incorporate the electrode in an expandable foam, such as an ear plug, to quickly place the electrode against a surface of the external auditory canal. In some embodiments, the housing of the neural stimulation device is conductive, and functions as the electrode.

Figure 3:
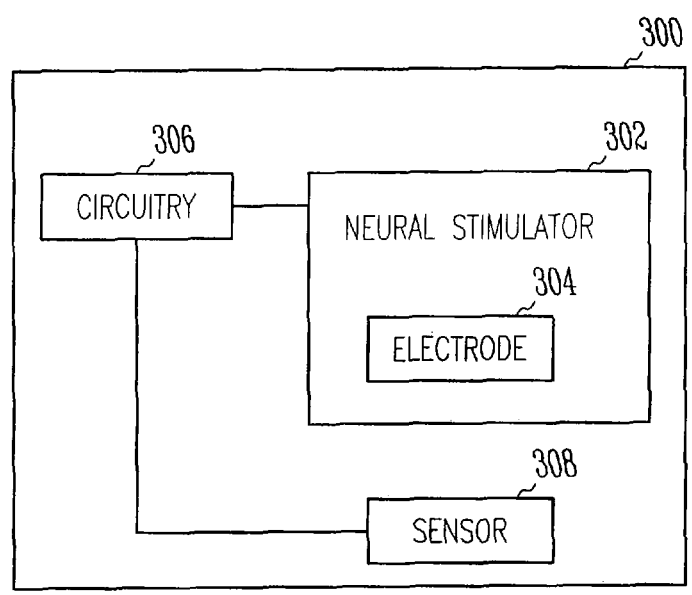
FIG. 3 illustrates a block diagram of various embodiments of a neural stimulation device.

FIG. 3 illustrates a block diagram of a neural stimulation device, such as device 203 of FIGS. 2A-2B, according to various embodiments. According to one embodiment, the device 300 includes a clip (as illustrated in FIG. 2B) adapted to detachably attach to the ear lobe. The device also includes a neural stimulator 302 including an electrode 304. The neural stimulator 302 is adapted to stimulate neural targets in the vicinity of the ear lobe. The neural stimulator is further adapted to communicate with a stimulation circuit 306 to receive a neural stimulation signal. The device also includes a sensor 308 adapted to monitor a physiological parameter. According to various embodiments, the sensor 308 may include an infrared sensor, such as pulse oximetry sensor, interstitial sensor and light-emitting diode (LED) sensor, for example. The sensor(s) may be configured to sense blood pressure, glucose, respiratory rate and/or heart rate. The device titrates therapy using the physiological parameter, according to various embodiments.

According to various embodiments, the sensor 308 includes a blood pressure sensor adapted to sense a parameter indicative of blood pressure, where the neural stimulation signal is adapted to chronically lower blood pressure using the sensed parameter. The neural stimulator delivers stimulation therapy using a preprogrammed schedule to chronically lower blood pressure, according to an embodiment. According to various embodiments, the sensor 308 includes a cardiac function sensor adapted to sense a parameter indicative of cardiac function, where the neural stimulation signal is adapted to improve cardiac function using the sensed parameter. The neural stimulator delivers stimulation therapy using a preprogrammed schedule to improve cardiac function, according to an embodiment. In one embodiment, the device 300 further includes a communication circuit. The communication circuit is adapted to communicate with an implantable and/or external device, in varying embodiments.

Figure 4:
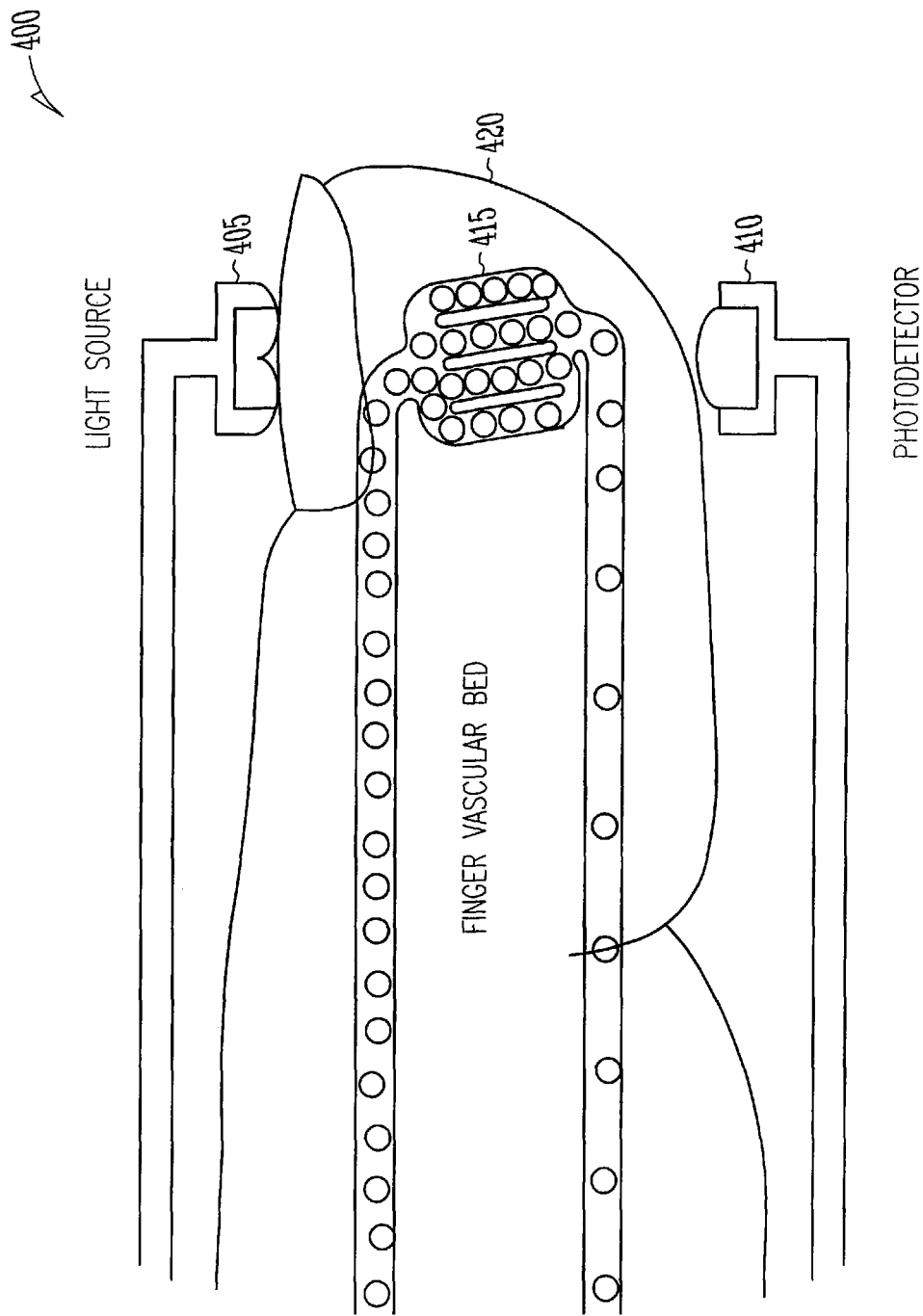
FIG. 4 illustrates an infrared sensor for use in a neural stimulation system, according to various embodiments.

FIG. 4 illustrates an infrared sensor 400 for use in a neural stimulation system, according to various embodiments. An example of an infrared sensor includes a pulse oximetry sensor, or other sensor for monitoring blood pressure, heart rate variability (HRV), glucose, respiratory rate, and/or heart rate. The sensor includes a light source 405 and a photodetector 410, according to an embodiment. The sensor is used to detect parameters in vessels 415 in extremities, such as a finger 420, toe, or ear lobe. In an embodiment, light absorption by hemoglobin differs depending upon the oxygen saturation, and pulse and oxygen saturation can be derived from the recorded signal (pulse oximetry embodiment). Other examples of infrared sensors may be implantable in various embodiments.

Figure 5:
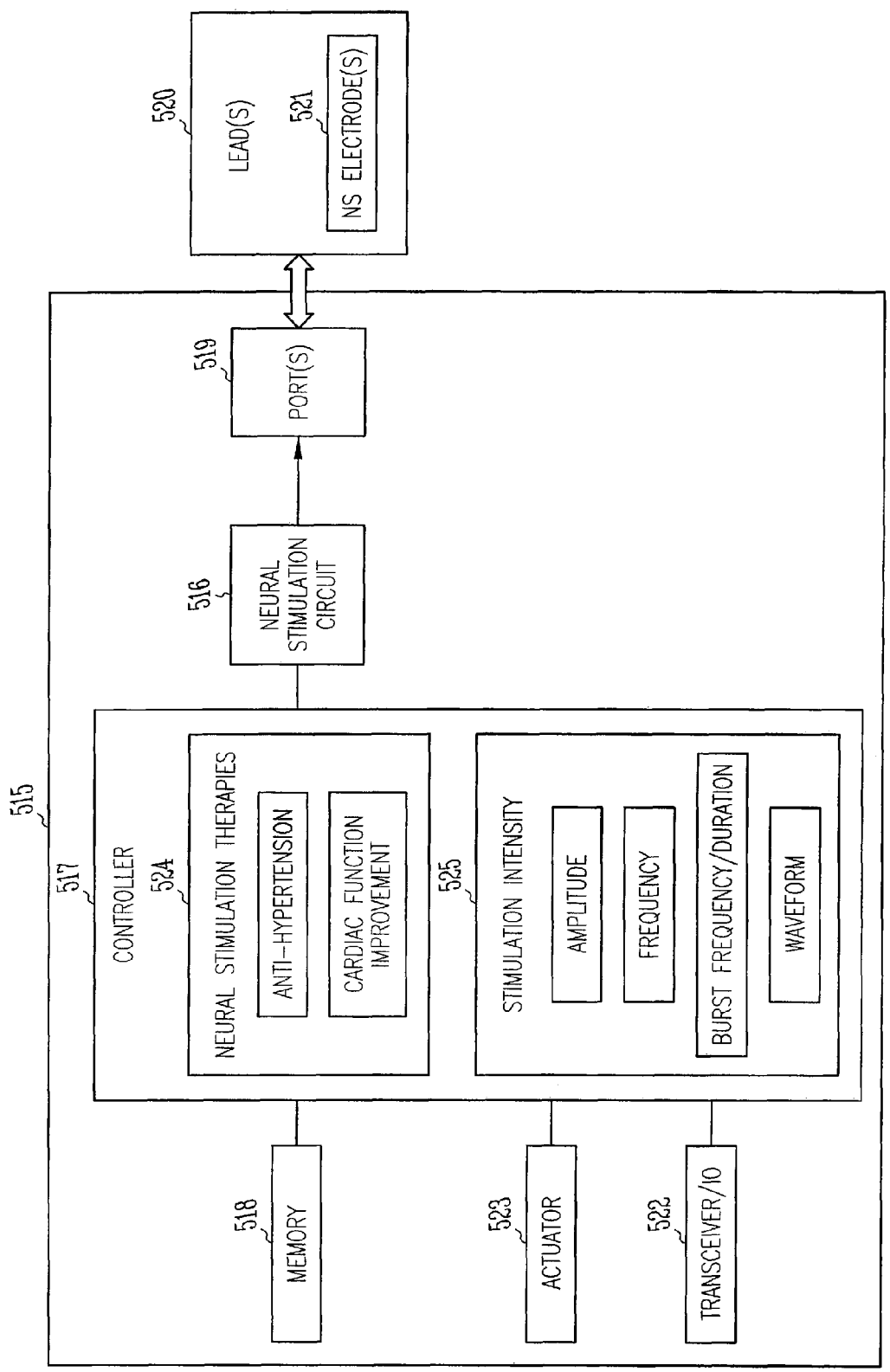
FIG. 5 illustrates various embodiments of a neural stimulator to stimulate neural targets in the vicinity of a human ear in an open loop stimulation system.

FIG. 5 illustrates a neural stimulator 515 to stimulate neural targets in the vicinity of a human ear in an open loop stimulation system, according to various embodiments. Such a neural stimulation device is capable of functioning as the open loop embodiment of stimulators 203 and 302 in FIGS. 2A and 3. The illustrated neural stimulator embodiment 515 includes a neural stimulation circuit 516, a controller 517, and memory 518. The illustrated embodiment further includes at least one port 519 to connect to at least one lead 520. Thus, for example, the lead(s) 520 is/are capable of detaching from the device 515, and other leads are capable of being used with the device. The neural stimulation circuit 516 is connected to the port(s) 519 to provide a neural stimulation signal to at least one neural stimulation electrode 521 on the lead(s) 520 to stimulate a neural target in the vicinity of a human ear when an appropriate signal is provided to an appropriately-positioned neural stimulation electrode or electrodes. Some embodiments stimulate the neural target using a single lead and a single electrode on the lead. However, multiple leads and multiple electrodes on the leads can be used. In various embodiments, the neural stimulation electrode 521 is designed to be clipped to an ear lobe. In various embodiments, the neural stimulation electrode 521 is designed to be positioned in an external auditory canal. In various embodiments, the neural stimulation electrode 521 is designed to be a transcutaneous electrode, such as a patch electrode, positioned on the skin of the head behind the ear and over or otherwise proximate to the ear. These ear placements are non-invasive. Implantable stimulators can also be used without departing from the scope of this disclosure. With non-invasive techniques, electrodes can be quickly positioned by a person who has minimal training, thus allowing therapy to be quickly applied. Thus, for example, therapy can be quickly applied in an emergency setting. These embodiments also provide a quick, non-invasive way for anti-hypertensive and/or cardiac function improvement therapy.

The illustrated neural stimulator 515 further includes a transceiver or other input/output (IO) circuit 522, and an actuator 523. The IO circuit allows the neural stimulator device to communicate with other devices, and thus can be used to program the neural stimulator device and/or upload historical neural stimulator data recorded over a period of time, for example. A wireless transceiver can be used to provide IO functions for both external and implantable devices. The actuator 523 provides a means for initiating a programmed therapy. Various actuator embodiments include a switch, such as mechanical, electrical, electronic and magnetic switches. The actuator can be triggered by a physician, emergency personal or a patient to initiate a preprogrammed therapy. Thus, in various embodiments, for example, a patient is capable of initiating angina therapy by positioning a magnet next to an implantable embodiment of the neural stimulator device.

The memory 518 includes computer-readable instructions that are capable of being operated on by the controller to perform functions of the device. Thus, in various embodiments, the controller is adapted to operate on the instructions to provide programmed stimulation therapies 524 such as anti-hypertensive and cardiac function improvement therapies. Additionally, in various embodiments, the controller is adapted to set parameters of the neural stimulation signal and, in some embodiments, vary parameters of the neural stimulation signal to adjust the intensity of the neural stimulation, such as is generally illustrated by the stimulation intensity module 525. Some embodiments control and/or vary the waveform, amplitude, frequency, burst frequency and duration, and some embodiments control and/or adjust various combinations of two or more of the waveform, amplitude, frequency, burst frequency and duration. Examples of waveforms include sinusoidal, square, triangular, and "white noise" signals. A white noise signal mimics naturally-occurring neural activity. Various "open loop" systems vary the intensity of the neural stimulation according to a preprogrammed therapy to provide a desired affect. For example, some embodiments vary parameters of the neural stimulation signal to prevent or reduce neural adaptation to the neural stimulation signal.

Figure 6:
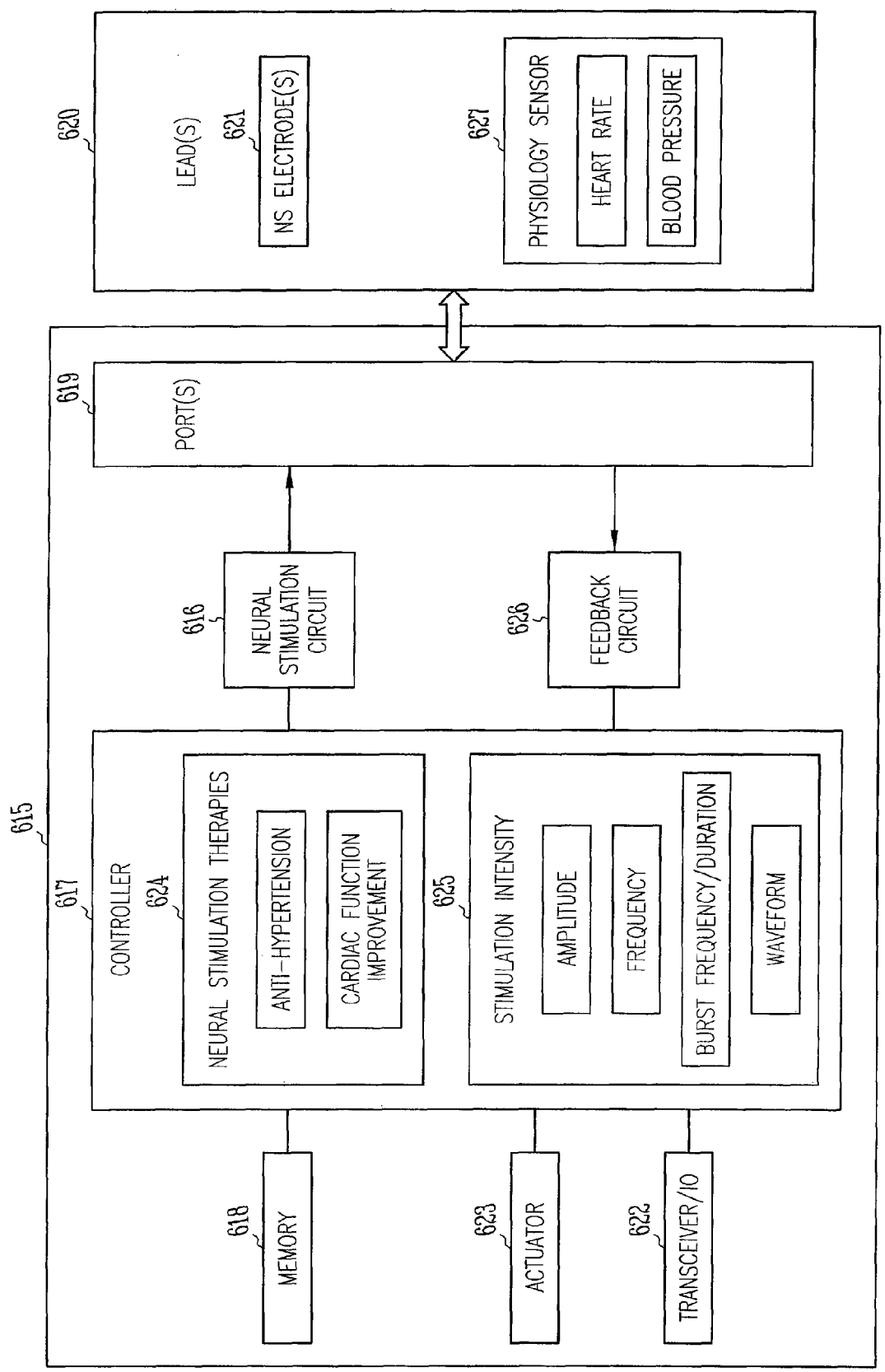
FIG. 6 illustrates a neural stimulator to stimulate neural targets in the vicinity of a human ear in a closed loop stimulation system, according to various embodiments.

FIG. 6 illustrates a neural stimulator to stimulate neural targets in the vicinity of a human ear in a closed loop stimulation system, according to various embodiments. Such a neural stimulation device is capable of functioning as the open loop embodiment of stimulators 203 and 302 in FIGS. 2A and 3. The illustrated neural stimulator embodiment 615 includes a neural stimulation circuit 616, a feedback circuit 626, a controller 617, and memory 618. The illustrated embodiment further includes at least one port 619 to connect to at least one lead 620. Thus, for example, the lead(s) is/are capable of detaching from the device, and other leads are capable of being used with the device. For example, one lead, which is connected to a first port, includes a neural stimulation electrode 621, and a second lead, which is connected to a second port, includes a physiology sensor 627. In another example, one lead, which is connected to one port, includes both a neural stimulation electrode 621 and a physiology sensor 627. Examples of physiology sensor 627 include, but are not limited to: infrared sensors such as a pulse oximetry sensor, or other sensor for monitoring blood pressure, heart rate variability (HRV), glucose, respiratory rate, and/or heart rate.

The neural stimulation circuit is connected to the port(s) to provide a neural stimulation signal to at least one neural stimulation electrode on the lead(s) to stimulate a neural target in the vicinity of a human ear when an appropriate signal is provided to an appropriately-positioned neural stimulation electrode. In various embodiments, the neural stimulation electrode 621 is designed to be clipped to an ear lobe. In various embodiments, the neural stimulation electrode 621 is designed to be positioned in an external auditory canal. In various embodiments, the neural stimulation electrode 621 is designed to be a transcutaneous electrode, such as a patch electrode, positioned on the skin of the head behind the ear and over or otherwise proximate to the ear. These ear placements are non-invasive. Implantable stimulators can also be used without departing from the scope of this disclosure.

The feedback circuit 626 is connected to the port(s) to receive a signal from the physiology sensor 627. The sensor senses a physiology function that depends, at least in part, on neural stimulation. Examples of such functions include heart rate and blood pressure. Thus, various embodiments implement a heart rate sensor as the physiology sensor, and various embodiments implement a blood pressure sensor as the physiology sensor. As stated, the physiology sensor includes an infrared sensor or pulse oximetry sensor, in various embodiments. The carotid artery runs proximate to the auricular nerve branch. Thus, various embodiments provide a sensor capable of directly detecting the heart rate from the carotid artery, and various embodiments provide a sensor capable of directly detecting blood pressure from the carotid artery. One example of such a sensor is an acoustic sensor adapted to sense blood flow. The sensed blood flow is capable of being used to determine blood pressure and/or heart rate. However, other sensor technology can be used. Transceiver 622, actuator 623, and memory 618 where previously discussed with respect to FIG. 5. This discussion is not repeated here for the sake of brevity.

The memory 618 includes computer-readable instructions that are capable of being operated on by the controller to perform functions of the device. Thus, in various embodiments, the controller is adapted to operate on the instructions to provide programmed neural stimulation therapies 624 such as anti-hypertensive and cardiac function improvement therapies. Various "closed loop" systems vary the intensity of the neural stimulation, as generally illustrated by the stimulation intensity module 625, based on the sensed physiology signal received by the feedback circuit according to a preprogrammed therapy to provide a desired affect. Thus, the closed loop system is capable of reducing and increasing the neural stimulation intensity as appropriate to maintaining some measured physiological parameters within an upper and lower boundary during the neural stimulation therapy.

Figure 7:
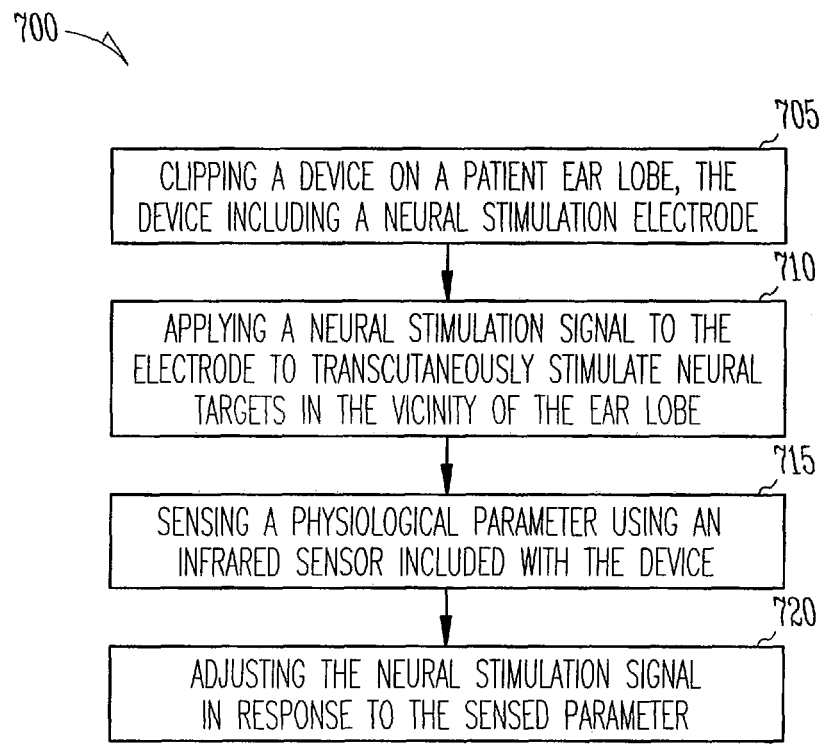
FIG. 7 illustrates an embodiment of a method for stimulating neural targets in the vicinity of a human ear.

FIG. 7 illustrates a method 700 for stimulating neural targets in the vicinity of a human ear, according to various embodiments. According to an embodiment, a device is clipped on a patient ear lobe at 705, the device including a neural stimulation electrode. At 710, a neural stimulation signal is applied to the electrode to transcutaneously stimulate neural targets in the vicinity of the ear lobe, according to an embodiment. At 715, a physiological parameter is sensed using a sensor connected to the device. The sensor includes an infrared sensor, in one embodiment. Other sensors, such as to sense blood pressure, glucose, respiratory rate and/or heart rate, can be used without departing from the scope of this disclosure. According to an embodiment, the neural stimulation signal is adjusted in response to the sensed parameter, at 720. According to various embodiments, the sensed physiological parameter includes a parameter indicative of blood pressure, and the neural stimulation signal is applied to chronically lower blood pressure using the sensed parameter. The physiological parameter includes a parameter indicative of cardiac function, and the neural stimulation signal is applied to improve cardiac function using the sensed parameter, according to various embodiments.

Figure 8:
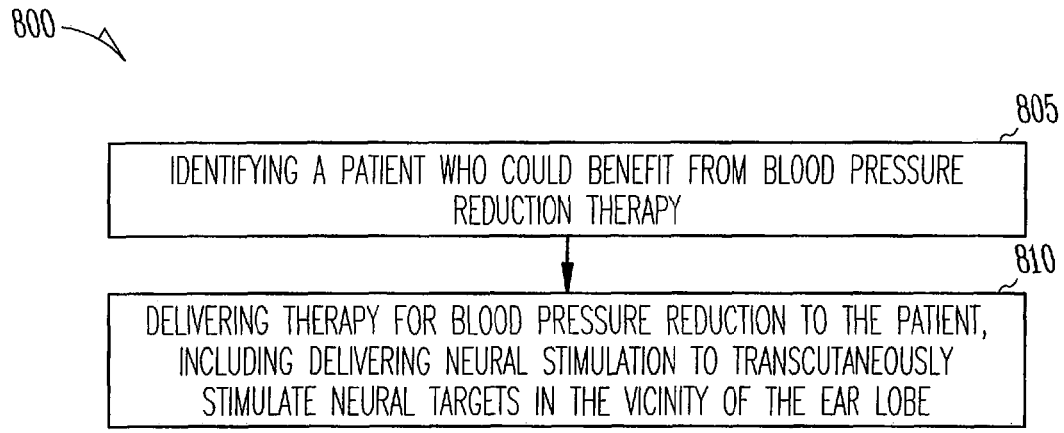
FIG. 8 illustrates a method for treatment of high blood pressure, according to various embodiments.

FIG. 8 illustrates a method 800 for treatment of high blood pressure, according to various embodiments. According to an embodiment, a patient is identified who could benefit from blood pressure reduction therapy, at 805. At 810, therapy for blood pressure reduction is delivered to the patient, including delivering neural stimulation to transcutaneously stimulate neural targets in the vicinity of the ear lobe, according to various embodiments. According to various embodiments, neural stimulation is delivered from a device that clips on to an ear lobe of a patient. Neural simulation is delivered to an auricular branch of a vagal nerve, in an embodiment. Other neural targets are used in varying embodiments. In one embodiment, a patient is identified for therapy using an external sensor. In another embodiment, a patient is identified for therapy using an implanted sensor. Blood pressure can be sensed using either an implanted or external sensor, and neural stimulation adjusted (frequency, duration, etc.) using the sensed blood pressure, in a closed loop system embodiment.

Figure 9:
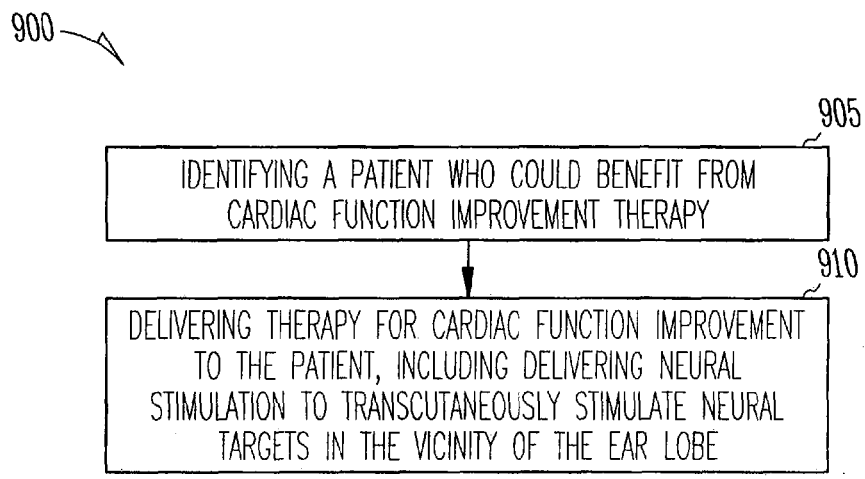
FIG. 9 illustrates an embodiment of a method for cardiac function improvement treatment.

FIG. 9 illustrates a method 900 for cardiac function improvement treatment, according to various embodiments. According to an embodiment, a patient is identified who could benefit from cardiac function improvement therapy, at 905. At 910, therapy for cardiac function improvement is delivered to the patient, including delivering neural stimulation to transcutaneously stimulate neural targets in the vicinity of the ear lobe, according to various embodiments. According to various embodiments, a patient is identified for therapy at least partially by sensing a parameter indicative of cardiac function. Examples of sensed parameters include, but are not limited to, respiratory rate, heart rate, and glucose level. According to an embodiment, a parameter indicative of cardiac function is sensed using a pulse oximetry sensor, or other infrared or LED sensor. Neural stimulation can be adjusted (frequency, duration, etc.) using the sensed parameter indicative of cardiac function, in a closed loop system embodiment.

Various embodiments of the methods of FIGS. 8 and 9 use a non-invasive technique to position the neural stimulation electrode, such as clipping the electrode on a patient ear lobe, positioning a bipolar electrode in the external auditory canal or positioning a transcutaneous electrode behind the ear and over the auricular nerve branch. Various embodiments use a minimally-invasive technique to position the neural stimulation electrode, such as subcutaneously implanting a neural stimulator and an electrode to stimulate the auricular nerve branch.

The illustrated methods 700, 800, 900 are capable of being stored as computer-readable instructions in a memory such as memory 518, 618, and operated on by controller such as controller 517, 617, in FIGS. 5, 6, to provide a desired neural stimulation therapy.

Although specific embodiments have been illustrated and described herein, it will be appreciated by those of ordinary skill in the art that any arrangement which is calculated to achieve the same purpose may be substituted for the specific embodiment shown. It is to be understood that the above description is intended to be illustrative, and not restrictive. The scope of the present subject matter should be determined with reference to the appended claims, along with the full scope of equivalents to which such claims are entitled.

We claim:

1. A device for mounting to an ear lobe of a patient, the device comprising:
 a clip configured to be clipped to the ear lobe;
 a neural stimulator connected to the clip and including:
  a neural stimulation circuit;
  a controller;
  a memory; and
  an electrode; and
 a sensor connected to the stimulation circuit, the sensor adapted to monitor a physiological parameter,
 wherein the controller is configured to control the neural stimulation circuit to stimulate neural targets in the vicinity of the ear lobe, including setting parameters of a neural stimulation signal, and further configured to titrate therapy using the physiological parameter, and
 wherein the clip, neural stimulator and sensor are configured such that the entire weight of the device is supported by the clip on the ear lobe.

2. The device of claim 1, wherein the sensor includes a blood pressure sensor adapted to sense a parameter indicative of blood pressure, wherein the neural stimulation signal is adapted to chronically lower blood pressure using the sensed parameter.

3. The device of claim 1, wherein the neural stimulator delivers stimulation therapy using a preprogrammed schedule to chronically lower blood pressure.

4. The device of claim 1, wherein the sensor includes a cardiac function sensor adapted to sense a parameter indicative of cardiac function, wherein the neural stimulation signal is adapted to improve cardiac function using the sensed parameter.

5. The device of claim 4, wherein the parameter indicative of cardiac function includes blood pressure.

6. The device of claim 4, wherein the parameter indicative of cardiac function includes heart rate.

7. The device of claim 4, wherein the parameter indicative of cardiac function includes heart rate variability (HRV).

8. The device of claim 1, wherein the neural stimulator delivers stimulation therapy using a preprogrammed schedule to improve cardiac function.

9. The device of claim 1, further comprising a communication circuit adapted to communicate with an implantable device.

10. The device of claim 1, wherein the sensor includes an infrared sensor.

11. A device for mounting to an ear lobe of a patient, the device comprising:
 a clip configured to be clipped to the ear lobe;
 a neural stimulator including an electrode in the clip, the neural stimulator adapted to stimulate neural targets in the vicinity of the ear lobe, the stimulator further adapted to communicate with a stimulation circuit to receive a neural stimulation signal;
 a memory adapted to store a programmed schedule for delivering neural stimulation; and
 a sensor connected to the stimulation circuit, the sensor adapted to monitor a physiological parameter,
 wherein the device titrates therapy using the physiological parameter, and
 wherein the clip, neural stimulator and sensor are configured such that the entire weight of the device is supported by the clip on the ear lobe.

12. The device of claim 11, wherein the memory includes computer-readable instructions that are capable of being operated on by a controller to perform functions of the device.

13. The device of claim 11, wherein the sensor includes a pulse oximetry sensor.

14. The device of claim 11, wherein the neural stimulator is adapted to stimulate an auricular branch of a vagal nerve.

15. The device of claim 11, wherein the sensor includes an acoustic sensor adapted to sense blood flow in a carotid artery.

16. A device for mounting to an ear lobe of a patient, the device comprising:
 a housing, wherein the housing is conductive and functions as an electrode;
 a clip configured to be clipped to the ear lobe;
 a neural stimulator within the housing connected to the clip, the neural stimulator connected to the electrode and adapted to stimulate neural targets in the vicinity of the ear lobe;

a stimulation circuit within the housing adapted to communicate with the neural stimulator to provide a neural stimulation signal; and a sensor connected to the stimulation circuit, the sensor adapted to monitor a physiological parameter, wherein the device titrates therapy using the physiological parameter, and wherein the clip, neural stimulator and sensor are configured such that the entire weight of the device is supported by the clip on the ear lobe.

17. The device of claim 16, wherein the neural stimulator includes a transceiver.

18. The device of claim 17, wherein die transceiver includes a wireless transceiver.

19. The device of claim 16, wherein the neural stimulator includes an actuator.

20. The device of claim 19, wherein the actuator is adapted to be used to initiate a programmed therapy.

* * * * *